US005851556A

United States Patent [19]

Breton et al.

[11] Patent Number: 5,851,556

[45] Date of Patent: Dec. 22, 1998

[54] USE OF A SALT OF AN ALKALINE-EARTH METAL AS TNF-A OR SUBSTANCE P INHIBITOR IN A TOPICAL COMPOSITION AND COMPOSITION OBTAINED

[75] Inventors: Lionel Breton, Versailles; Olivier De Lacharriere, Paris, both of France

[73] Assignee: Société L'Oréal S.A., Paris, France

[21] Appl. No.: 630,326

[22] Filed: Apr. 10, 1996

[30] Foreign Application Priority Data

| | | | |
|---|---|---|---|
| Apr. 10, 1995 | [FR] | France | 95 04264 |
| Apr. 10, 1995 | [FR] | France | 95 04265 |
| Apr. 10, 1995 | [FR] | France | 95 04267 |
| Apr. 10, 1995 | [FR] | France | 95 04268 |
| Sep. 20, 1995 | [FR] | France | 95 10980 |

[51] Int. Cl.[6] .................... A61K 33/32

[52] U.S. Cl. .................... 424/639; 424/600; 424/617; 424/646; 424/650; 424/677; 424/715; 424/718; 424/722

[58] Field of Search .................... 424/722, 600, 424/617, 639, 646, 650, 677, 715, 718

[56] References Cited

U.S. PATENT DOCUMENTS

| | | | |
|---|---|---|---|
| 3,519,711 | 7/1970 | Svigals | 424/659 |
| 3,772,431 | 11/1973 | Mlkvy et al. | 424/44 |
| 3,888,976 | 6/1975 | Mlkvy et al. | 424/44 |
| 4,477,439 | 10/1984 | D'Alelio (deceased) | 424/162 |
| 4,735,802 | 4/1988 | Le | 424/682 |
| 4,943,432 | 7/1990 | Biener | 424/647 |
| 4,980,184 | 12/1990 | Gordon | 424/53 |
| 4,986,981 | 1/1991 | Glace et al. | 424/50 |
| 5,047,409 | 9/1991 | Di Schiena et al. | 514/275 |
| 5,079,010 | 1/1992 | Natterer | 424/617 |
| 5,091,171 | 2/1992 | Yu et al. | 424/642 |
| 5,202,130 | 4/1993 | Grant et al. | 424/617 |
| 5,296,476 | 3/1994 | Henderson | 514/163 |
| 5,593,992 | 1/1997 | Adams et al. | 514/235.8 |

FOREIGN PATENT DOCUMENTS

| | | |
|---|---|---|
| 0 401 503 | 4/1990 | European Pat. Off. . |
| 0451300 | 10/1991 | European Pat. Off. . |
| 0459890 | 12/1991 | European Pat. Off. . |
| 0 522 808 | 7/1992 | European Pat. Off. . |
| 0586929 | 3/1994 | European Pat. Off. . |
| 2122613 | 9/1972 | France . |
| 4315866 | 5/1994 | Germany . |
| 1072355 | 6/1964 | United Kingdom . |
| 2271774 | 4/1994 | United Kingdom . |
| WO 83/01252 | 4/1983 | WIPO . |
| WO87/01935 | 10/1986 | WIPO . |
| WO93/01165 | 7/1992 | WIPO . |
| WO93/14084 | 7/1993 | WIPO . |
| 94/09798 | 5/1994 | WIPO . |
| WO 96/19184 | 6/1996 | WIPO . |

OTHER PUBLICATIONS

*Nordia Briefs,* "A Salt–Containing Cream for Dry Skin", No. 484, Jan. 1978.

*The United States Pharmacopeia,* "Alumina/Drug Substances and Dosage Form", pp. 20 and 22 (1975).

Maison G. deNavarre, *The Chemistry and Manufacture of Cosmetics,* 2nd Ed. vol. IV, p. 1261 (1975).

Alexander A. Fisher, "Irritant Reactions from Topical Urea Preparations Used for Dry Skin Advantages of a Urea–Free 'Dead Sea Salt' Cream", *Current Contact News,* vol. 18, pp. 761–772 (1976).

Rajadhyaksha, *Chemical Abstracts,* vol. 107, 1987, #223281.

Di Schiena, *Chemical Abstracts,* vol. 106, 1987, #107768.

Smith et al., *Chemical Abstracts,* vol. 114, 1991, #206554.

Dufetal et al., *Chemical Abstracts,* vol. 116, 1992, #135998.

S.M. Moussaoui et al, *Br. J. Pharmacol.,* "A non–peptide $NK_1$–receptor antagonist, RP 67580, inhibits neurogenic inflammation postsynaptically", vol. 109, No. 1, 1993, pp. 259–265.

J. Wallengren, *Br. J. Dermatol.,* "Substance P antagonist inhibits immediate and delayed type cutaneous hypersensitivity reactions", vol. 124, No. 4, 1991 pp. 324–328.

J. Wallengren et al, *Contact Dermatitis,* "Some neuropeptides as modulators of experimental contact allergy", vol. 19, No. 5, 1988, pp. 351–354.

T. Lotti et al., *J. Am. Acad. Dermatol.,* "Treatment of aquagenic pruritus with topical capsaicin cream", vol. 30, No. 2PT1, Feb. 1994, pp. 232–235.

T. Sakurada et al, *Brain Res.,* "A selective and extremely potent antagonist of the neurokinin–1 receptor", vol. 593, No. 2, 1992, pp. 319–322.

K. Folkers et al, *Proc. Natl. Acad. Sci. USA,* "Spantide II, an effective tachykinin antangonist having high potency", vol. 87, No. 12, 1990, pp. 4833–4855.

Janscro–Gabor, "Action of rare earth metal complexes on neurogenic as well as on bradykinin–induced inflammation", *J. Pharm. Pharmac.*, 22:366–371 (1970).

Dec. 6, 1995; Cosmetologie, *Therapeutique*, No. 1511, Dec. 17, 19995.

Uy Dong Sohn et al, "Agonist–Independent, Muscle–Type–Specific Signal Transduction Pathways in Cat Esophageal and Lower Esophageal Sphincter Circular Smooth Muscle", *J. of Pharmacology & Experimental Therapeutics*, 273:481–491 (1995).

(List continued on next page.)

*Primary Examiner*—Shelley A. Dodson
*Assistant Examiner*—Michael A. Williamson
*Attorney, Agent, or Firm*—Burns, Doane, Swecker & Mathis, L.L.P.

[57] ABSTRACT

The invention relates to the use of a salt of an alkaline-earth metal in a cosmetic, pharmaceutical, veterinary and/or dermatological composition for treating, in particular, sensitive skins. It relates, in addition, to the use of a salt of an alkaline-earth metal for preventing and/or combating rosacea and/or skin irritation and/or dartre and/or pudic erythema and/or dysesthetic sensation and/or sensation of inflammation and/or pruritus of the skin and/or of the mucous membranes. The salt is in particular strontium nitrate or chloride.

87 Claims, No Drawings

OTHER PUBLICATIONS

Mitsuo Ishizawa, "Contractile Responses of Longitudinal Muscle Strip to 5–HT and Influences of Divalent Cations in the Guinea–Pig Isolated Colon", *J. Smooth Muscle Res.*, 30:65–72 (1994).

H. Goodman, *Cosmetic Dermatology,* First Edition, Fourth Impression, p. 181 (1936).

*Martindale,* The Extra Pharmacopoeia, Twenty–seventh Edition, The Pharmaceutical Press, London, pp. 219, 1775 and 1814 (1977).

Sohn et al, Different Receptors Activate a Different Single G–Protein in Esophageal. (Gis) and in LES (Gq) Circular Smooth Muscle, *Gastroenterology,* vol. 104 (1993).

British Medical Journal (England), vol. 4, Nov. 1975, p. 264.

Chemical Abstracts, vol. 122, No. 16, Apr. 1995, Columbus, Ohio, abstract No. 196540.

Chemical Abstracts, vol. 95, No. 22, Nov. 1981, Columbus, Ohio, abstract No. 192217.

Chemical Abstracts, vol. 120, No. 17, Apr. 1994, Columbus, Ohio, abstract No. 210122.

USE OF A SALT OF AN ALKALINE-EARTH METAL AS TNF-A OR SUBSTANCE P INHIBITOR IN A TOPICAL COMPOSITION AND COMPOSITION OBTAINED

The present invention relates to the use of alkaline-earth metal salts and more particularly of a strontium salt in a cosmetic, pharmaceutical, veterinary and/or dermatological composition as well as to the composition obtained. More particularly, these salts make it possible to treat, via the topical route, pathological and/or physiological disorders associated with the release of substance P and/or of TNF-alpha (Tumour Necrosis Factor-alpha) and especially to treat sensitive skins, skin disorders and skin diseases involving a pruritus, rosacea and pudic erythema.

It is known that some skins are more sensitive than others. The symptoms of sensitive skins were up until now poorly characterized and the problem of these skins was, as a result, poorly defined; no-one knew exactly the process involved in the sensitivity—nonallergic cutaneous hyperactivity—of the skin. Some thought that a sensitive skin was a skin which reacted with cosmetic and/or dermatological products, others that it was a skin which reacted with several external factors, not necessarily linked to cosmetic and/or dermatological products.

Some tests have been tried in order to endeavour to define sensitive skins, for example tests with lactic acid or with DMSO which are known to be irritant substances: see for example the article by K. Lammintausta et al., Dermatoses, 1988, 36, pages 45–49; and the article by T. Agner and J. Serup, Clinical and Experimental Dermatology, 1989, 14, pages 214–217. However, these tests did not make it possible to characterize sensitive skins.

Moreover, sensitive skins were assimilated to allergic skins.

Because the characteristics of sensitive skins were poorly known, it was up until now very difficult to treat them, and they were treated indirectly, for example, by limiting in cosmetic and/or dermatological compositions the use of products with an irritant character such as surfactants, preservatives and perfumes as well as the use of some additives.

The applicant has performed numerous clinical test and it has been able to determine the symptoms linked to sensitive skins. These symptoms are in particular subjective signs which are essentially dysesthetic sensations. Dysesthetic sensations are understood to mean sensations which are painful to a greater or lesser degree and which are felt in a skin area, such as pricking, formication, itching, pruritus, burning, inflammation, discomfort, stabbing pain and the like.

The applicant has been able to show, in addition, that a sensitive skin was not an allergic skin. Indeed, an allergic skin is a skin which reacts to an external agent, an allergen, which initiates an allergic reaction. It is an immunological process which occurs only when an allergen is present and which affects only sensitive subjects. The essential characteristic of sensitive skin is, according to the applicant, on the contrary, a mechanism of response to external factors, which may involve any individual, even though the so-called individuals with sensitive skin react thereto more rapidly than others. This mechanism is not immunological, it is aspecific.

The applicant has now found that sensitive skins can be separated into two main clinical forms, irritable skins and intolerant skins.

An irritable skin is a skin which reacts through a pruritus, that is to say through itching or pricking, to various factors such as the environment, emotions, food, wind, rubbing, razor, hard water with a high concentration of limestone, variations in temperature or wool. In general, these signs are associated with a dry skin with or without dartres, or with a skin which has an erythema.

An intolerant skin is a skin which reacts by sensations of inflammation, stabbing pain, formication and/or reddening, to various factors such as the application of cosmetic or dermatological products or of soap. In general, these signs are associated with an erythema and with a hyperseborrheic or acneic skin, or even rosaceiform skin, with or without dartres.

In general, sensitive skins are defined by a specific reactivity of the skin. This hyperreactivity can especially be brought into play by environmental, emotional or dietary factors or alternatively by the application of or the contact with cosmetic or dermatological products. This hyperreactivity state, which defines sensitive skins differentiates the latter from the ubiquitous reactivity caused by irritant agents which induce an irritation of the skin in practically all individuals.

This hyperreactivity state is felt and recognized by individuals affected by it as a “sensitive skin”.

“Sensitive” scalps have a clinical semiology which is more univocal: the sensations of pruritus and/or of pricking and/or of inflammation are essentially initiated by local factors such as rubbing, soap, surfactants, hard water with a high limestone concentration, shampoos or lotions. These sensations are also sometimes initiated by factors such as the environment, emotions and/or food. An erythema and a hyperseborrhoea of the scalp as well as a dandruff state are frequently associated with the preceding signs.

Moreover, in some anatomical regions such as the large skin-folds (inguinal, genital, axillary, popliteal, anal, submammary regions and elbow bends) and the feet, sensitive skin results in pruriginous sensations and/or dysesthetic sensations (inflammation, pricking) linked in particular to sweat, rubbing, wool, surfactants, hard water with a high limestone concentration and/or variations in temperature.

To determine whether a skin is sensitive or not, the applicant has also developed a test. Indeed, after having performed a large number of tests with the aim of defining a sensitive skin, it found surprisingly that there was a link between persons with sensitive skin and those who reacted to a topical application of capsaicin.

The capsaicin test consists in applying over about 4 $cm^2$ of skin 0.05 ml of a cream containing 0.075% capsaicin and in noting the appearance of subjective signs caused by this application, such as pricking, burning and itching. In subjects with sensitive skins, these signs appear between 3 and 20 minutes after the application and are followed by the appearance of an erythema which starts at the periphery of the area of application.

Capsaicin was used as medicinal product, in particular for treating pain of the zona. Capsaicin causes a release of neuropeptides from the sensitive nerve fibres in particular tachykinins such as substance P and CGRP (peptide derived from the calcitonin gene: Calcitonin Gene Related Peptide) which come from nerve endings of the epidermis and the dermis. The applicant observed that the physiopathological pattern common to all the states of sensitive skins was linked to a high capacity to release neuropeptides and more particularly tachykinins and CGRP in the skin. The dysesthetic manifestations which are caused by their release are termed “neurogenic”.

It is known, in addition, that the neuropeptides released by the sensitive epidermal endings induce a cascade of biochemical events including the release of pro-inflammatory mediators among which are the Tumor Necrosis Factor-alpha (TNF-α), histamine, interleukin-1, interleukin-6 and interleukin-8.

Substance P is a polypeptide chemical element produced and released by a nerve ending. It is involved especially in the transmission of pain and in diseases of the central nervous system such as anxiety, schizophrenia, in respiratory and inflammatory diseases, in gastrointestinal diseases, in rheumatic diseases and in some dermatological diseases such as eczema, atopic dermatitis, psoriasis and acne.

CGRP is also a polypeptide chemical element produced and released by a nerve ending. It is involved especially in respiratory and inflammatory diseases, in allergic and rheumatic diseases and in some dermatological diseases such as eczema, urticaria, contact dermatitis or prurigo.

The applicant has now discovered that one of the essential characteristics of sensitive skins, cutaneous intolerance and irritation reactions, was linked to the release of neuropeptides and/or pro-inflammatory mediators such as TNF-α and that the molecules which prevented the release of these neuropeptides and/or the release of TNF-α could make it possible to obtain a preventive and/or curative effect for sensitive skins.

Moreover, the applicant has found surprisingly that alkaline-earth metal salts were inhibitors of TNF-alpha and that some of these salts were, furthermore, antagonists of substance P.

Through application FR-A-2,719,476 of 5 May, 1994, filed in the name of the applicant, it is known to use substance P antagonists which prevent the synthesis and/or the release and/or the attachment of substance P to treat sensitive skins. However, alkaline-earth metal salts are not listed as substance P antagonists capable of treating sensitive skins.

To treat sensitive skins, the applicant has therefore envisaged using alkaline-earth metal salts especially as TNF-alpha inhibitors. It has indeed been observed, surprisingly, that the incorporation of an alkaline-earth metal salt into a cosmetic and/or dermatological composition made it possible to avoid the irritation and/or the dysesthetic sensations and/or the pruritus of the skin and/or of the mucous membranes, especially by reducing the release of neuropeptides in the skin and/or the mucous membranes.

No one had up until now established a link between alkaline-earth metal salts and sensitive skin. The clinical signs of sensitive skin are essentially subjective: pricking, formication, pruritus, stabbing pain, inflammation and they are sometimes combined with erythmas. These signs are due to aspecific external factors. The symptoms seem essentially localized to the face, the neck and the scalp, but may also appear on the whole body.

Pruritus is a symptom which causes a discomfort which is often considerable for the patient; when the pruritus is very severe, the discomfort may be such that the patient cannot pursue his normal activity. In addition, the pruritus may be a source of complications: abrasions which may become super-infected, lichenification of the pruriginous areas, which have the consequence of placing the disease in a real vicious circle.

Pruritus is not only associated with sensitive skins but also with skin disorders such as atopic dermatitis, contact dermatitis, lichen planus, prurigo, urticaria, pruriginous toxidermia and some clinical forms of psoriasis.

Furthermore, pruritus is sometimes the predominant cutaneous pathological sign as in the cases of aquagenic pruritus, pruritus of the scalp in dandruff states (*Pityriasis capitis*), pruritus of a haemodialysed patient, of renal insufficiency patients, of AIDS patients and of persons affected by biliary obstructions, or alternatively of pruritus of paraneoplastic manifestations of certain cancers.

Up until now, pruritus was treated with the aid of emollient preparations, local corticoids, puvatherapy or alternatively antihistaminics. Local corticoids are indeed very effective for alleviating the symptoms but unfortunately their effect is not immediate. Furthermore, they have side effects which are often highly detrimental, such as atrophies, and they present risks of mycotic and/or bacterial and/or viral infections. Puvatherapy is the local irritation of the diseased skin with UVAs, after absorption of a photosensitizing substance (psoralene). This technique has the serious disadvantages of a photoaging which can cause skin cancers. Furthermore, this treatment is not ambulatory, which obliges the patients to visit a specialist centre often during the entire treatment, which is very constraining and limits their professional activity.

Emollients have a very low anti-pruriginous effect and are not very effective when the pruritus is considerable. Moreover, antihistaminics do not have a constant efficacy and require oral administration.

The need therefore remains for a treatment of these pruriginous conditions which does not have these disadvantages.

The subject of the present invention is therefore the use of at least one salt of an alkaline-earth metal for treating pruritus effectively, while overcoming the abovementioned disadvantages.

No one had up until now envisaged treating pruritus symptomatically by means of salts of an alkaline-earth metal.

As other skin disorder related to sensitive skins, there may also be mentioned rosacea which is a skin condition characterized by an erythema of the face which is predominant on the cheeks, the forehead, the nose, a hyperseborrhoea of the face in the region of the forehead, the nose and the cheeks, and by an infectious component with acneform pustules.

Moreover, associated with these signs is a cutaneous hyperreactivity characterized by the appearance of reddening and of subjective sensations of the itching or pruritus type, of sensations of burning or inflammation, of sensations of pricking, formication, discomfort, stabbing pain and the like.

These signs of hyperreactivity can be initiated by a wide range of factors such as the consumption of food or of hot or alcoholic drinks, by rapid variations in temperature, by heat and especially exposure to ultraviolet or infrared radiation, by a low relative humidity, by exposure of the skin to violent winds or to air currents (fan, air conditioner), by the application of surfactants or the use of certain cosmetics even when these are not known to be particularly irritant.

The applicant has found that these signs, and especially erythrosic erythema characteristic of rosacea, were linked to a neurogenic inflammatory component.

Up until now, the mechanism of initiation of these signs was very poorly known and rosacea was treated with active agents such as antiseborrheic and antiinfectious agents, for example benzoyl peroxide, retinoic acid, metronidazole or the cyclines, which act on the infection and the hyperseborrhoea, but which do not make it possible to treat the neurogenic component of this condition, and especially the hyperreactivity of the skin and the reddening.

Likewise, there was up until now no treatment for the reddening which appears in pudic erythema. The latter is caused by emotion and is characterized by reddening of the face and of the neck and shoulders, which may be accompanied by a pruritus (itching). This condition is very uncomfortable for persons suffering from it, and up until now it could only be treated with beta-blockers, potent drugs used for treating hypertension and having numerous contraindications.

The need therefore remains for a treatment of skin reddening and of the hyperreactivity state of skin affected by rosacea or pudic erythema.

The subject of the present invention is precisely the use of one or more alkaline-earth metal salts for treating this skin reddening.

No one had up until now envisaged using alkaline-earth metal salts for treating skin reddening of neurogenic origin.

The subject of the present invention is therefore the use of at least one salt of at least one alkaline-earth metal in or for the manufacture of a composition containing a cosmetically, pharmaceutically and/or dermatologically acceptable medium for treating sensitive human skins and/or human skin reddening of neurogenic origin, reddening more particularly due to the release of tachykinins.

The application of compositions containing one or more alkaline-earth metal salts makes it possible to obtain a marked decrease or even a complete disappearance of the reddening which manifests itself both in rosacea and in pudic erythema.

The alkaline-earth metal salt therefore acts on the neurogenic component of these conditions, for which there was no treatment up until now, and thus enhances the efficacy of the active agents used up until now for the treatment of their infectious component, especially in the case of rosacea.

The subject of the present invention is also the use of at least one salt of at least one alkaline-earth metal for preventing and/or combating rosacea, and/or pudic erythema, skin irritation and/or dartre and/or erythema and/or sensation of inflammation and/or dysesthetic sensation and/or pruritus of the skin and/or of the mucous membranes of humans.

Pruritus should be understood to mean the pruriginous symptoms of disorders and/or diseases of the skin or of the mucous membranes. The salts of the invention are intended for the treatment of pruritus and not for the treatment of the disorders and/or diseases responsible for this pruritus.

The subject of the present invention is therefore also the use of at least one salt of an alkaline-earth metal in or for the preparation of a cosmetic, pharmaceutical or dermatological composition for treating the pruriginous symptoms of the disorders and/or diseases of the skin.

The subject of the invention is also the use of at least one salt of at least one alkaline-earth metal as TNF-alpha inhibitor in or for the manufacture of a composition containing a cosmetic, pharmaceutical, dermatological or veterinary medium.

The subject of the invention is also the use of at least one salt of at least one alkaline-earth metal as TNF-alpha inhibitor, in or for the manufacture of a composition containing a cosmetically, pharmaceutically or dermatologically acceptable medium, for treating sensitive skins.

The subject of the invention is also the use of at least one salt of at least one alkaline-earth metal as TNF-alpha inhibitor, in or for the manufacture of a cosmetic, pharmaceutical, dermatological or veterinary composition intended for the treatment of pathological and/or physiological disorders associated with the release of TNF-alpha.

For a substance to be recognized as a TNF-alpha inhibitor, it should correspond especially to at least one of the following characteristics:

inhibition of the release of TNF-alpha by monocytes (U937 cells) stimulated by a phorbol ester (PMA)

inhibition of the attachment of TNF-alpha to its membrane receptor.

The TNF-alpha inhibitors according to the invention can, in addition, be used for treating especially fever, septic shock and/or cachexia.

A cosmetically, physiologically, pharmaceutically and/or dermatologically acceptable medium is a medium which is compatible with the skin, the scalp, the nails and the mucous membranes of humans. The composition containing one or more salts of one or more alkaline-earth metals can therefore be applied to the face, the neck, the hair and the nails, or any other skin area of the human body such as the large skin-folds (axillary regions, submammary regions, elbow bends, and the like), the mucous membranes (anal, genital, nasal).

A veterinary or even physiological medium is a medium which is compatible with the skin, the claws and the mucous membranes of animals.

According to the invention, it is possible to use one or more alkaline-earth metal salts. As salts which can be used in the invention, there may be mentioned barium, calcium, magnesium, strontium and/or beryllium salts. The salts of the invention may be anhydrous or hydrated.

These salts may be for example carbonates, bicarbonates, sulphates, glycerophosphates, borates, chlorides, nitrates, acetates, hydroxides, persulphates as well as salts of α-hydroxy acids (citrates, tartrates, lactates, malates) or of fruit acids, or alternatively salts of amino acids (aspartate, arginate, glycoholate, fumarate) or salts of fatty acids (palmitate, oleate, caseinate, behenate). Preferably, the salt is chosen from calcium, strontium or magnesium nitrate, borate, chloride, sulphate and acetate.

Still more advantageously, the salt is a magnesium and, even better, a strontium salt provided especially in the form of,a chloride or a nitrate.

The strontium and, to a less degree, magnesium salts are substance P antagonists.

For a substance to be recognized as a substance P antagonist, it should correspond especially to the following characteristic:

have a substance P-antagonizing pharmacological activity, that is to say induce a coherent pharmacological response in at least one of the following two tests:
  - the antagonist substance should reduce the extravasation of the plasma across the vascular wall which is induced by capsaicin or by an antidromic nerve stimulation, or alternatively,
  - the antagonist substance should cause inhibition of the contraction of the smooth muscles induced by the administration of substance P.

Moreover, the substance P-antagonizing substance may have a selective affinity for the NK1 receptors for tachykinins.

The applicant observed, surprisingly, that the strontium salts had the characteristic of inhibiting the receptor attachment of substance P and could therefore be used as receptor antagonists of substance P.

Accordingly, the subject of the invention is also the use of at least one strontium salt in a physiologically acceptable medium in and/or for the manufacture of a cosmetic, dermatological, pharmaceutical and/or veterinary composition intended for treating pathological and/or physiological disorders associated with the release of substance P.

The physiological disorders associated with substance P are especially skin conditions (atopic dermatitis, psoriasis, eczema, acne, urticaria, neurodermatitis, prurigo, sensitive skins, pruritus), bronchopulmonary conditions (asthma, allergic bronchitis, allergic rhinitis), pain (dental, ophthalmic, tympanic, rheumatic and post-traumatic pain and migraine), gastrointestinal conditions and diseases of the central nervous system (depression, schizophrenia).

Accordingly, the subject of the invention is also the use of at least one strontium salt in a physiologically acceptable medium in and/or for the manufacture of a cosmetic, dermatological, pharmaceutical and/or veterinary composition intended for treating skin conditions, bronchopulmonary conditions, pain, gastrointestinal conditions and/or diseases of the central nervous system.

The subject of the invention is also the use of at least one strontium salt in a physiologically acceptable medium in and/or for the manufacture of a cosmetic, dermatological, pharmaceutical and/or veterinary composition intended for treating atopic dermatitis, eczema, psoriasis and acne.

In the compositions according to the invention, the alkaline-earth metal salt is preferably used in a quantity representing from 0.001 to 30% of the total weight of the composition, and in particular in a quantity representing from 0.01 to 20% of the total weight of the composition and even better from 0.5 to 10%.

The subject of the invention is also a cosmetic, pharmaceutical or veterinary process for inhibiting the attachment and/or the synthesis and/or the release of TNF-alpha in the skin, characterized in that there is applied to the skin, the scalp and/or the mucous membranes a composition containing at least one salt of at least one alkaline-earth metal in a cosmetic, pharmaceutical or veterinary medium.

The subject of the present invention is, in addition, a process for the cosmetic and/or dermatological treatment of sensitive skins and/or of skin reddening of neurogenic origin, characterized in that there is applied to the skin, the scalp and/or the mucous membranes which are sensitive and/or which are affected by rosacea a composition as described above containing at least one salt of at least one alkaline-earth metal in a cosmetically and/or dermatologically acceptable medium.

The subject of the present invention is, in addition, a process for the cosmetic and/or dermatological treatment of the pruriginous symptoms of disorders and/or diseases of the skin and/or of the mucous membranes, characterized in that there is applied to the skin, the scalp and/or the mucous membranes a composition as described above containing at least one salt of at least one alkaline-earth metal in a cosmetically and/or dermatologically acceptable medium.

The subject of the invention is also a process for the cosmetic and/or dermatological treatment of the physiological disorders associated with the release of substance P, characterized in that there is applied to the skin, the scalp and/or the mucous membranes a composition containing at least one strontium salt as defined above in a cosmetically and/or dermatologically acceptable medium.

Advantageously, there is combined with the alkaline-earth metal salts one or more antagonists of one or more neuropeptides, these antagonists being preferably receptor antagonists, and/or one or more antagonists of one or more inflammation mediators.

Accordingly, the subject of the invention is also a cosmetic, pharmaceutical, veterinary and/or dermatological composition containing, in a cosmetic, pharmaceutical, veterinary and/or dermatological medium, at least one salt of at least one alkaline-earth metal and at least one neuropeptide antagonist and/or at least one inflammation mediator antagonist, different from the said salts, especially for treating sensitive skins.

As neuropeptide antagonists which can be used in the invention, there may be mentioned the antagonists of substance P and the antagonists of CGRP and, as inflammation mediator antagonists, there may be mentioned the antagonists of histamine, of interleukin-1 or of TNF$\alpha$. These antagonists may be present in an amount of 0.000001 to 10% of the total weight of the composition and, even better, from 0.0001 to 5%.

Advantageously, antagonists which are preferably receptor antagonists of substance P, of CGRP and/or of interleukin-1 are used.

As substance P antagonist which can be used in the invention, there may be mentioned any substance of organic or inorganic origin, capable of producing an inhibition of the receptor attachment of substance P or an inhibition of the synthesis and/or the release of substance P by sensitive nerve fibres.

The receptor antagonist of substance P may be especially a peptide or a non-peptide derivative comprising a heteroatom, and more precisely a compound comprising a heterocycle or a heteroatom linked directly or indirectly to a benzene ring.

Sendide and Spantide II can be used, for example, as receptor antagonist peptide of substance P.

It is also possible to use in the invention, as peptide, those described in the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide receptor antagonists of substance P which can be used in the invention are especially heterocyclic compounds, especially sulphur-containing, nitrogen-containing or oxygen-containing compounds or compounds comprising a nitrogen atom linked directly or indirectly to a benzene ring.

As heterocyclic compound, there may be used in the invention those described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen-containing heterocycle is a 2-tricyclyl-2-aminoethane derivative, a spirolactam derivative, a quinuclidin derivative, an azacyclic derivative, an aminopyrrolidine derivative, a piperidine derivative, an aminoazaheterocycle or an isoindole derivative.

As compounds comprising a nitrogen atom linked directly or indirectly to a benzene nucleus, there may be mentioned those described in the following documents: EP-A-522808 and WO-A-93/01165.

As antagonist of CGRP which can be used in the invention, there may be mentioned any substance of organic or inorganic origin capable of producing an inhibition of the receptor attachment of CGRP or of producing an inhibition of the synthesis and/or of the release of CGRP by the sensitive nerve fibres.

For a substance to be recognized as a CGRP antagonist, it should correspond especially to the following characteristic:

have a CGRP-antagonizing pharmacological activity, that is to say induce a coherent pharmacological response especially in one of the following tests:

the antagonist substance should reduce the vasodilation induced by capsaicin and/or the antagonist substance should cause an inhibition of the release of CGRP by the sensitive nerve fibres and/or the antagonist substance should cause an inhibition of the contraction of the smooth muscle of the deferent channel induced by CGRP.

In addition, the CGRP antagonist may have an affinity for the CGRP receptors.

It is possible to use in the invention, for example, as receptor antagonist of CGRP, CGRP 8-37, an anti-CGRP antibody.

The compositions according to the invention can be applied either via the local route, that is to say via the topical route or by subcutaneous and/or intradermal injection, or via the systematic or general route, that is to say via the oral route and/or by intramuscular injection.

The compounds according to the invention can be provided in any galenic forms normally used according to the route of administration (topical, injectable or ingestible application).

The injectable compositions may be provided in the form of an aqueous or oily lotion or in the form of a serum.

The compositions used via the oral route may be provided in the form of capsules, gelatin capsules, syrups or tablets.

For a topical application, the compositions may be provided especially in the form of aqueous, aqueous-alcoholic or oily solutions, of dispersions of the solution type or dispersions of the lotion or serum type, emulsions of liquid or semi-liquid consistency of the milk type, obtained by dispersion of a fatty phase in an aqueous phase (O/W) or conversely (W/O), or of suspensions or emulsions of soft, semi-solid or solid consistency of the cream type, of an aqueous or anhydrous gel, or alternatively of microemulsions, microcapsules, microparticles, or vesicular dispersions of the ionic and/or nonionic type.

These compositions are prepared according to the customary methods.

They can also be used for the hair in the form of aqueous, alcoholic or aqueous-alcoholic solutions, or in the form of creams, gels, emulsions, foams or alternatively in the form of compositions for aerosol also containing a pressurized propelling agent.

The quantities of the various constituents of the compositions according to the invention are those conventionally used in the fields considered.

These compositions constitute especially creams for the cleansing, protection, treatment or care for the face, for the hands, for the feet, for the large anatomical skin-folds or for the body (for example day creams, night creams, make-up removing creams, foundation creams, antisun creams), make-up products as fluid foundations, make-up removing milks, body milks for protection or care, aftersun milks, lotions, gels or foams for skin care, such as cleansing or disinfecting lotions, antisun lotions, artificial tanning lotions, bath compositions, deodorant compositions containing a bactericidal agent, aftershave gels or lotions, depilatory creams, compositions against insect bites, anti-pain compositions or compositions for treating certain skin diseases such as severe pruritus, rosacea, acne, ulcers of the leg, psoriasis, pustules, vibex.

The compositions according to the invention may also consist of solid preparations constituting cleansing cakes or soaps.

The salt of an alkaline-earth metal can also be incorporated into various compositions for hair care, especially shampoos, optionally antiparasitic shampoos, hair setting lotions, treatment lotions, hair-styling gels or creams, dyeing compositions (especially oxidation dyes) optionally in the form of colouring shampoos, hair restructuring lotions, compositions for permanent waving (especially compositions for the first stage of a permanent waving), lotions or gels for preventing hair loss, and the like.

The compositions of the invention may also be for dentibuccal use, for example a toothpaste or a mouthwash. In this case, the compositions may contain customary adjuvants and additives for compositions for buccal use and especially surfactants, thickening agents, humectants, polishing agents such as silica, various active ingredients such as fluorides, in particular sodium fluoride, and optionally sweeteners such as sodium saccharinate.

When the composition of the invention is an emulsion, the proportion of fatty phase may range from 5% to 80% by weight, and preferably from 5% to 50% by weight relative to the total weight of the composition. The oils, emulsifiers and coemulsifiers used in the composition in the form of emulsion are chosen from those conventionally used in the cosmetic and/or dermatological field. The emulsifier and the coemulsifier are present, in the composition, in a proportion ranging from 0.3% to 30% by weight, and preferably from 0.5 to 20% by weight relative to the total weight of the composition. The emulsion may, in addition, contain lipid vesicles.

While the composition of the invention is a solution or an oily gel, the fatty phase may represent more than 90% of the total weight of the composition.

In a known manner, the cosmetic and/or dermatological composition of the invention may also contain adjuvants which are customary in the cosmetic, pharmaceutical and/or dermatological field, such as hydrophilic or lipophilic gelling agents, hydrophilic or lipophilic active agents, preservatives, antioxidants, solvents, perfumes, fillers, screening agents, bactericides, odour absorbers and colouring matter. The quantities of these various adjuvants are those conventionally used in the field considered, and are for example from 0.01% to 20% of the total weight of the composition. These adjuvants, depending on their nature, can be introduced into the fatty phase, into the aqueous phase and/or into the lipid spherules.

As fatty substances which can be used in the invention, there may be mentioned mineral oils (hydrogenated polyisobutene, liquid paraffin), vegetable oils (liquid fraction of shea butter, sunflower oil, apricot kernel oil), animal oils (perhydrosqualene), synthetic oils (Purcellin oil, isopropyl myristate, ethylhexyl palmitate), and fluorinated oils (perfluoropolyethers). It is also possible to use fatty alcohols, fatty acids (stearic acid), waxes (paraffin, carnauba, beeswax).

It is also possible to use silicone compounds such as silicone oils (cyclomethicon, dimethicon), waxes, resins and gums. These compounds may be functionalized or not.

As emulsifiers which can be used in the invention, there may be mentioned for example glycerol stearate, polysorbate 60, the cetylstearyl alcohol/oxyethylenated cetylstearyl alcohol mixture containing 33 mol of ethylene oxide (Sinnowax AO sold by the company Henkel), the PEG-6/PEG-32/Glycol Stearate mixture sold under the name Tefose® 63 by the company Gattefosse, PPG-3 myristyl ether, silicone emulsifiers such as cetyldimethicone copolyol and sorbitan mono-or tristearate, PEG-40 stearate, oxyethylenated sorbitan monostearate (20EO).

As solvents which can be used in the invention, there may be mentioned lower alcohols, especially ethanol and isopropanol and propylene glycol.

As hydrophilic gelling agents, there may be mentioned carboxyvinyl polymers (carbomer), acrylic copolymers such as acrylate/alkyl acrylate copolymers, polyacrylamides and especially the mixture of polyacrylamide, C13-14 isoparaffin and Laureth-7 sold under the name Sepigel 305 by the company Seppic, polysaccharides (cellulose derivatives) such as hydroxyalkyl celluloses (hydroxypropyl cellulose, hydroxyethyl cellulose), natural gums (guar, carob, xanthan) and clays, and, as lipophilic gelling agents, there may be mentioned modified clays such as bentones, metal salts of fatty acids such as aluminium stearate and hydrophobic silica, or alternatively ethyl cellulose (cellulose derivatives) and polyethylene.

As hydrophilic active agents, it is possible to use proteins or protein hydrolysates, amino acids, polyols especially $C_2$ to $C_{10}$ (glycerine, sorbitol, butylene glycol, polyethylene glycol), urea, allantoin, sugars and sugar derivatives, water-soluble vitamins, starch, bacterial or plant extracts such as those of Aloe vera.

As lipophilic active agents, it is possible to use retinol (vitamin A) and its derivatives, tocopherol (vitamin E) and its derivatives, essential fatty acids, ceramides and essential oils.

It is possible, inter alia, to combine the alkaline-earth metal salts with active agents intended especially for the prevention and/or the treatment of skin conditions.

Among these active agents, there may be mentioned by way of example:

- agents modulating the differentiation and/or proliferation and/or pigmentation of the skin, such as retinoic acid and its isomers, retinol and its esters, retinal, retinoids, especially those described in the documents FR-A-2 570 377, EP-A-199636, EP-A-325540, EP-A-402072, vitamin D, and its derivatives, oestrogens such as estradiol, kojic acid or hydroquinone;
- antibacterial agents such as clindamycin phosphate, erythromycin or the tetracycline class of antibiotics;
- antiparasitic agents, in particular metronidazole, crotamiton or pyrethrinoids;
- antifungal agents, in particular the compounds belonging to the imidazole class such as econazole, ketoconazole or miconazole or their salts, polyene compounds, such as amphotericin B, compounds of the allylamine family, such as terbinafin, or alternatively octopirox;
- steroidal anti-inflammatory agents, such as hydrocortisone, anthralins (dioxyanthranol), anthranoids, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;
- anaesthetic agents such as lidocain hydrochloride and its derivatives;
- antipruriginous agents such as thenaldine, trimeprazine or cyproheptadine;
- antiviral agents such as acyclovir;
- keratolytic agents such as alpha- and beta-hydroxycarboxylic or beta-ketocarboxylic acids, their salts, amides or esters and more particularly hydroxy-acids such as glycolic acid, lactic acid, maleic acid, salicylic acid, citric acid and in general fruit acids and 5-(n-octanoyl)salicylic acid;
- anti-free radical agents, such as alpha-tocopherol or its esters, superoxide dismutases, certain metal chelators or ascorbic acid and its esters;
- antiseborrheic agents such as progesterone;
- antidandruff agents such as octopirox or zinc pyrithione;
- antiacne agents such as retinoic acid or benzoyl peroxide;
- antimetabolites;
- agents for combating hair loss such as monoxidil;
- antiseptics
- corticoids.

It is known that corticoids are effective for the treatment of eczema, but that their use often causes undesirable side effects. Now, the combination with the strontium salt used according to the invention makes it possible to reduce or even eliminate the corticoid level while allowing good efficacy on the eczema.

In addition, the composition of the invention may contain, advantageously, a thermal and/or mineral water, especially chosen from Vittel water, Vichy basin waters, Uriage water, Roche Posay water, Bourboule water, Enghien-les-bains water, Saint-Gervais-les-bains water, Neris-les-bains water, Allevard-les-bains water, Digne water, Maizieres water, Neyrac-les-bains water, Lons le Saunier water, Eaux Bonnes, Rochefort water, Saint Christau water, Fumades water and Tercis-les-bains water. It is preferably Roche Posay water.

The process for cosmetic and/or dermatological treatment of the invention can be carried out especially by applying the hygiene or cosmetic and/or dermatological compositions as defined above, according to the usual technique for using these compositions. For example, application of make-up removing creams, gels, sera, lotions or milks or of aftersun compositions to the skin or to dry hair, application of a hair lotion to wet hair, of shampoos, or alternatively application of toothpaste to the gums.

Tests have revealed the activity of various strontium salts as substance P antagonists with reference to Spantide II, which is known as substance P antagonist, and in comparison with another alkaline-earth metal salt, calcium nitrate.

The test consisted in determining the activity of the various compounds on the release of substance P, caused by antidromic stimulation of the sciatic nerve. This release is visualized by staining with a dye (Evans blue). The greater the quantity of substance P released, the more intense the colour. In other words, the greater the inhibitory effect produced on this release by the substance P antagonist, the less intense the colour.

The results are presented in Tables 1 and 2 below:

TABLE 1

| | Control vehicle | Spantide II 30 nmol | $Sr(NO_3)_2$ 1 $\mu$mol | $SrCl_2$ 1 $\mu$mol | $Ca(NO_3)_2$ 1 $\mu$mol |
|---|---|---|---|---|---|
| $\mu$g/ml of Evans blue | 8.19 ± 0.83 | 4.35 ± 0.46 | 4.84 ± 0.6 | 5.13 ± 0.9 | 11.25 ± 1.77 |
| % inhibition relative to the control | — | 47% | 41% | 37% | — |
| Statistics | — | $p < 0.01$ | $p < 0.05$ | $p < 0.05$ | not significant |

It is evident from this Table 1 that the strontium salts have a substantial inhibitory activity on the release of substance P whereas the calcium salt, at the same concentration level, does not have any activity at all.

TABLE 2

| | Control vehicle | Spantide II 30 nmol | $Sr(NO_3)_2$ 1 μmol | $SrCl_2$ 1 μmol | $Ca(NO_3)_2$ 10 μmol |
|---|---|---|---|---|---|
| μg/ml of Evans blue | 6.26 ± 1.09 | 3.63 ± 0.69 | 1.80 ± 0.68 | 2.71 ± 0.67 | 8.45 ± 1.55 |
| % inhibition relative to the control | — | 42% | 71% | 57% | — |
| Statistics | — | $p < 0.05$ | $p < 0.001$ | $p < 0.01$ | not significant |

It is evident from this Table 2 that the strontium salts have a substantial inhibitory activity on the release of substance P whereas the calcium salt has no activity at all, even at a higher concentration level.

The following test makes it possible to show that the alkaline-earth metal salts and more particularly magnesium, strontium or calcium chloride as well as strontium nitrate are inhibitors of TNF-alpha.

This test is performed on human monocytes (U937 line) stimulated by a phorbol ester (PMA) according to the method described by Schindler et al (Correlations and interactions in the production of interleukin-6 (IL-6), IL-1, and Tumor Necrosis Factor (TNF) in human blood mononuclear cells: IL-6 suppresses IL-1 and TNF. Blood 75: 40–47 (1990)).

The phorbol ester (PMA) naturally stimulates the synthesis and/or the secretion of TNF-alpha by human monocytes in culture.

The activity of the molecules is evaluated according to their ability to reduce or even eliminate this TNF-alpha secretion.

The cells (monocytes) are incubated in the presence of PMA at the concentration of 10 nM for 48 hours at 37° C. The quantities of TNF-alpha secreted are quantified by immuno-enzymatic assay (ECA) with the aid of commercially available kits.

Each molecule is tested at 3 different concentrations ($10^{-5}$, $10^{-4}$ and $10^{-3}$M) and during each experiment, a reference molecule (dexamethasone) is studied at 7 concentrations as internal standard.

The results are expressed as percentage inhibition relative to the positive control (without test molecule) after subtracting the background noise. A recapitulative Table 3 groups together the mean inhibitory effects obtained with the compounds. (The results expressed in % inhibition; they are the mean of 3 measurements).

The $IC_{50}$ value (50% reduction in the secretion, caused by PMA) is calculated, for the reference molecule, from the competition curve according to a non-linear regression model.

TABLE 3

| test | compounds | $10^{-5}$M | $10^{-4}$M | $10^{-3}$M | reference | $IC_{50}$ |
|---|---|---|---|---|---|---|
| % inhibition of | $SrCl_2 7H_2O$ | 14 | — | 54 | dexamethasone | 4 × $10^{-9}$M |
| | $MgCl_2$ | — | 12 | 70 | | |
| | $CaCl_2,7H_2O$ | 19 | 22 | 67 | | |
| TNF-alpha secretion induced by PMA | $Sr(NO_3)_2$ | — | 28 | 75 | | |

It is observed that the inhibition of TNF-alpha increases with the salt concentration.

The following examples illustrate compositions for topical application in accordance with the invention. In these examples, the proportions indicated are by weight.

EXAMPLE 1

Make-up removing lotion for the face for sensitive skins

| | |
|---|---|
| Magnesium chloride | 3.00 |
| Antioxidant | 0.05 |
| Isopropanol | 40.00 |
| Preservative | 0.30 |
| Water | qs 100% |

EXAMPLE 2

Make-up removing lotion for the face for sensitive skins

| | |
|---|---|
| CGRP 8-37 | 0.10 |
| Calcium nitrate | 2.00 |
| Antioxidant | 0.05 |
| Isopropanol | 40.00 |
| Preservative | 0.30 |
| Water | qs 100% |

EXAMPLE 3

Face care milk for sensitive skins

| | |
|---|---|
| Magnesium chloride | 5.00 |
| Glycerol stearate | 1.00 |
| Cetylstearyl alcohol/oxyethylenated cetylstearyl alcohol containing 33 mol EO (Sinnowax AO sold by the company Henkel) | 3.00 |
| Cetyl alcohol | 1.00 |
| Dimethicone (DC 200 Fluid sold by the company Dow Corning) | 1.00 |
| Liquid paraffin | 6.00 |
| Isopropyl myristate (Estol IPM 1514 sold by Unichema) | 3.00 |
| Antioxidant | 0.05 |
| Glycerin | 20.00 |
| Preservative | 0.30 |

EXAMPLE 4

Face care gel for sensitive skins

| | |
|---|---|
| Barium nitrate | 4.00 |
| Hydroxypropyl cellulose (Klucel H sold by the company Hercules) | 1.00 |
| Spantide II | 0.50 |
| CGRP 8-37 | 0.05 |
| Antioxidant | 0.05 |

-continued

| | |
|---|---|
| Isopropanol | 40.00 |
| Preservative | 0.30 |
| Water | qs 100% |

EXAMPLE 5

Face care gel for sensitive skins

| | |
|---|---|
| Magnesium nitrate | 5.00 |
| Hydroxypropyl cellulose (Klucel H from Hercules) | 1.00 |
| Antioxidant | 0.05 |
| Isopropanol | 40.00 |
| Preservative | 0.30 |
| Water | qs 100% |

EXAMPLE 6

Shampoo for sensitive scalp

| | |
|---|---|
| Sodium lauryl ether sulphate (2.2 EO) | 12.00 |
| Strontium chloride | 5.00 |
| Hydroxypropyl cellulose (Klucel H from Hercules) | 1.00 |
| Perfume | 0.50 |
| Preservative | 0.30 |
| Water | qs 100% |

EXAMPLE 7

O/W emulsion for the care of sensitive skins against insect bites or rosacea

| | |
|---|---|
| Cyclomethicone | 3.00 |
| Purcellin oil (sold by the company Dragocco) | 7.00 |
| PEG-6/PEG-32/Glycol Stearate (Tefose ® 63 from Gattefosse) | 0.30 |
| Strontium chloride | 3.00 |
| Preservative | 0.30 |
| Perfume | 0.40 |
| Carbomer | 0.60 |
| Crotamiton | 5.00 |
| Glycyrrhetinic acid | 2.00 |
| Ethanol | 5.00 |
| Triethanolamine | 0.20 |
| Water | gs 100% |

EXAMPLE 8

Antipain gel

| | |
|---|---|
| Strontium nitrate | 3.00 |
| Hydroxypropyl cellulose (Klucel H from Hercules) | 1.00 |
| Antioxidant | 0.05 |
| Lidocaine hydrochloride | 2.00 |
| Isopropanol | 40.00 |
| Preservative | 0.30 |
| Water | qs 100% |

EXAMPLE 9

Face care O/W emulsion for sensitive skins

| | |
|---|---|
| Strontium nitrate | 0.25 |
| Glycerol stearate | 2.00 |
| Polysorbate 60 (Tween 60 sold by the company ICI) | 1.00 |
| Stearic acid | 1.40 |
| Metronidazole | 1.00 |
| Triethanolamine | 0.70 |
| Sendide | 0.50 |
| Carbomer | 0.40 |
| Liquid fraction of shea butter | 12.00 |
| Liquid paraffin | 12.00 |
| Antioxidant | 0.05 |
| Perfume | 0.5 |
| Preservative | 0.30 |
| Water | qs 100% |

EXAMPLE 10

Solar erythema treatment fluid for sensitive skins (oil-in-water emulsion)

| | |
|---|---|
| Strontium chloride | 4.00 |
| Glycerol stearate | 2.00 |
| Polysorbate 60 (Tween 60 sold by the company ICI) | 1.00 |
| Stearic acid | 1.40 |
| Glycyrrhetinic acid | 2.00 |
| Triethanolamine | 0.70 |
| Carbomer | 0.40 |
| Liquid fraction of shea butter | 12.00 |
| Sunflower oil | 10.00 |
| Antioxidant | 0.05 |
| Preservative | 0.30 |
| Water | qs 100% |

EXAMPLE 11

Anti-pruriginous treatment lotion for genital mucous membranes

| | |
|---|---|
| Strontium chloride | 6 |
| Antioxidant | 0.05 |
| Isopropanol | 40 |
| Preservative | 0.3 |
| Water | qs 100% |

EXAMPLE 12

Treatment gel for moderate pruritus

| | |
|---|---|
| Strontium chloride | 4 |
| Hydroxypropyl cellulose (Klucel H sold by the company Hercules) | 1 |
| Antioxidant | 0.05 |
| Isopropanol | 40 |
| Preservative | 0.3 |
| Water | qs 100% |

EXAMPLE 13

Body gel for the treatment of severe pruritus during dermatosis

| | |
|---|---|
| Sendide | 0.2 |
| Strontium nitrate | 5 |

-continued

| | |
|---|---|
| Hydroxypropyl cellulose (Klucel H) | 1 |
| Antioxidant | 0.05 |
| Isopropanol | 40 |
| Preservative | 0.3 |
| Water | qs 100% |

EXAMPLE 14

Treatment cream for facial rosacea (oil-in-water emulsion)

| | |
|---|---|
| Magnesium chloride | 5.00% |
| Glycerol stearate | 2.00% |
| Polysorbate 60 (Tween 60 sold by the company ICI) | 1.00% |
| Stearic acid | 1.40% |
| Triethanolamine | 0.70% |
| Carbomer | 0.40% |
| Cyclomethicone | 8.00% |
| Sunflower oil | 12.00% |
| Antioxidant | 0.05% |
| Preservative | 0.30% |
| Water | qs 100% |

EXAMPLE 15

Gel for rosacea

| | |
|---|---|
| All-trans-retinoic acid | 0.05% |
| Calcium sulphate | 5.00% |
| Hydroxypropyl cellulose (Klucel H sold by the company Hercules) | 1.00% |
| Antioxidant | 0.05% |
| Isopropanol | 40.00% |
| Preservative | 0.30% |
| Water | qs 100% |

EXAMPLE 16

Gel for pudic erythema

Example 16 is identical to Example 15, except that it contains, in addition, 0.3% sendide.

EXAMPLE 17

Cream for rosacea (oil-in-water emulsion)

| | |
|---|---|
| Magnesium sulphate | 3.00% |
| Glycerol stearate | 2.00% |
| Polysorbate 60 (Tween 60 sold by the company ICI) | 1.00% |
| Stearic acid | 1.40% |
| Metronidazole | 0.50% |
| Triethanolamine | 0.70% |
| Carbomer | 0.40% |
| Cyclomethicone | 8.00% |
| Sunflower oil | 10.00% |
| Antioxidant | 0.05% |
| Preservative | 0.30% |
| Water | qs 100% |

EXAMPLE 18

Cream for rosacea (oil-in-water emulsion)

| | |
|---|---|
| Magnesium chloride | 4.00% |
| Glycerol stearate | 2.00% |
| Spantide | 0.50% |
| CGRP 8-37 | 0.25% |
| Polysorbate 60 (Tween 60 sold by the company ICI) | 1.00% |
| Stearic acid | 1.40% |
| Triethanolamine | 0.70% |
| Carbomer | 0.40% |
| Cyclomethicone | 8.00% |
| Sunflower oil | 12.00% |
| Antioxidant | 0.05% |
| Preservative | 0.30% |
| Water | qs 100% |

EXAMPLE 19

Treatment cream for atopic dermatitis outside eczematous growths

| | |
|---|---|
| Ethylhexyl palmitate | 3.00% |
| Liquid fraction of shea butter (palmitic-stearic-oleic-linoleic acid triglycerides) | 2.00% |
| Glycerol stearate | 3.00% |
| Sorbitan tristearate (Span 65 from ICI) | 0.90% |
| Hydrogenated polyisobutene | 4.50% |
| Vitamin E | 0.02% |
| Volatile silicone oil | 5.00% |
| PEG-40 stearate (Myrj 52) | 2.00% |
| Sodium PCA | 6.00% |
| Disodium EDTA | 0.05% |
| Strontium chloride | 10.00% |
| Glycerine | 3.00% |
| Preservative | 0.30% |
| Sepigel 305 | 1.00% |
| Water | qs 100% |

EXAMPLE 20

Treatment cream for atopic dermatitis during eczematous growths

| | |
|---|---|
| Ethylhexyl palmitate | 3.00% |
| Liquid fraction of shea butter (palmitic-stearic-oleic-linoleic acid triglycerides) | 2.00% |
| Glycerol stearate | 3.00% |
| Sorbitan tristearate (Span 65 from ICI) | 0.90% |
| Hydrogenated polyisobutene | 4.50% |
| Vitamin E | 0.02% |
| Volatile silicone oil | 5.00% |
| PEG-40 stearate (Myrj 52) | 2.00% |
| Sodium PCA | 6.00% |
| Disodium EDTA | 0.05% |
| Strontium chloride | 5.00% |
| Beta-methasone 17-valerate (corticoid) | 0.05% |
| Glycerine | 3.00% |
| Preservative | 0.30% |
| Sepigel 305 | 1.00% |
| Water | qs 100% |

EXAMPLE 21

Treatment lotion for eczema

| | |
|---|---|
| Strontium nitrate | 5.00% |
| Glycerol stearate | 1.00% |
| Cetylstearyl alcohol/oxyethylenated cetylstearyl alcohol containing 33 mol EO (Sinnowax AO sold by the company Henkel) | 3.00% |
| Cetyl alcohol | 1.00% |
| Volatile silicone oil | 1.00% |
| Liquid paraffin | 6.00% |

-continued

| | |
|---|---|
| Isopropyl myristate | 3.00% |
| Glycerine | 20.00% |
| Preservative | 0.30% |
| Water | qs 100% |

EXAMPLE 22

O/W emulsion intended for the treatment of acne

| | |
|---|---|
| Fatty phase: | |
| Apricot kernel oil | 14.50% |
| Liquid fraction of shea butter (palmitic-stearic-oleic-linoleic acid triglycerides) | 8.00% |
| Sorbitan monostearate (Span 60 from ICI) | 2.50% |
| Purcellin oil | 2.00% |
| Aqueous phase: | |
| Preservatives | 0.50% |
| Disodium salt of ethylenediaminetetra-acetic acid $2H_2O$ (complexing agent) | 0.05% |
| Neutralizing agent | 0.50% |
| Gelling agent | 0.70% |
| Glycerine | 5.00% |
| Oxyethylenated sorbitan monostearate (20 EO) (Tween 60 from ICI) (surfactant) | 2.50% |
| Strontium chloride | 1.00% |
| Roche-Posay water | 60.00% |
| Demineralized or deionized water | qs 100% |

EXAMPLE 23

Moisturising milk for the face

| | |
|---|---|
| Strontium chloride | 5.00% |
| Glycerol stearate | 1.00% |
| Cetylstearyl alcohol/oxyethylenated cetylstearyl alcohol containing 33 mol EO (Sinnowax AO sold by the company Henkel) | 3.00% |
| Cetyl alcohol | 1.00% |
| Polydimethylsiloxane (DC 200 Fluid sold by the company Dow Corning) | 1.00% |
| Liquid paraffin | 6.00% |
| Isopropyl myristate (Estol IPM 1514 sold by Unichema) | 3.00% |
| Antioxidant | 0.05% |
| Glycerine | 20.00% |
| Preservative | 0.30% |
| Water | qs 100% |

EXAMPLE 24

Treatment cream for solar erythema for sensitive skins (O/W emulsion)

| | |
|---|---|
| Strontium chloride | 4.00% |
| Glycerol stearate | 2.00% |
| Polysorbate 60 (Tween 60 sold by the company ICI) | 1.00% |
| Stearic acid | 1.40% |
| Glycyrrhetinic acid | 2.00% |
| Triethanolamine | 0.70% |
| Carbomer | 0.40% |
| Liquid fraction of shea butter | 12.00% |
| Sunflower oil | 10.00% |
| Antioxidant | 0.05% |
| Perfume | 0.50% |

-continued

| | |
|---|---|
| Preservative | 0.30% |
| Water | qs 100% |

We claim:

1. Cosmetic, dermatological, veterinary or pharmaceutical composition containing, in a cosmetic, dermatological, veterinary or pharmaceutical medium, at least one salt of at least one alkaline-earth metal which alkaline earth metal inhibits TNF-alpha activity and at least one neuropeptide antagonist or at least one inflammation mediator antagonist, different from the said salt.

2. Composition according to claim 1, wherein the salt is selected from the group consisting of chlorides, carbonates, borates, nitrates, acetates, hydroxides, sulfates, the salts of fruit acids and the amino acid salts.

3. Composition according to either of claims 1 and 2, wherein the salt is selected from the group consisting of calcium, magnesium, strontium, beryllium and barium containing salts.

4. Composition according to claim 1, wherein the salt is a magnesium or strontium salt.

5. Composition according to claim 1, wherein the salt is strontium chloride or strontium nitrate.

6. Composition according to claim 1, wherein the neuropeptide antagonist is selected from the group consisting of receptor antagonists of substance P, antagonists CGRP and interleukin-1 antagonists.

7. Composition according to claim 1, wherein the neuropeptide or inflammation mediator antagonist comprises from 0.000001 to 10% of the total weight of the composition.

8. Composition according to claim 1, wherein the alkaline-earth metal salt comprises from 0.01 to 30% of the total weight of the composition.

9. Composition according to claim 1, wherein the alkaline-earth metal salt comprises from 0.01 to 20% of the total weight of the composition.

10. Composition according to claim 1, which contains, in addition, at least one agent different from the said salts, selected from the group consisting of antibacterial, antiparasitic, antifungal, anti-inflammatory, antiseptic, antipruriginous, anaesthetic, antiviral, keratolytic, anti-free radical, antiseborrheic, antidandruff and anti-acne agents, corticoids and agents which modulate at least one of differentiation, proliferation or pigmentation of the skin.

11. Composition according to claim 1, wherein the cosmetically or dermatologically acceptable medium is an aqueous, oily or aqueous-alcoholic solution, a water-in-oil emulsion, an oil-in-water emulsion, a microemulsion, an aqueous gel, an anhydrous gel, a serum, and a dispersion of vesicles microcapsules or of microparticles.

12. Composition according to claim 1, wherein the medium contains, in addition, at least one of mineral and thermal water.

13. Composition according to claim 1, which contains at least one active agent chosen from proteins or protein hydrolysates, amino acids, polyols, urea, sugars and sugar derivatives, vitamins, starch, plant extracts, essential fatty acids, ceramides, essential oils and hydroxy acids.

14. Composition according to claim 1, which contains, in addition, at least one adjuvant chosen from fatty substances, silicones, hydrophilic gelling agents, lipophilic gelling agents, preservatives, perfumes, antioxidants, solvents, fillers, screening agents, odor absorbers and coloring matter.

15. Composition according to claim 14, wherein the gelling agents are cellulose derivatives.

16. Composition according to claim 1, which is suitable for the cleansing, care, protection, treatment of, application of make-up to and removal of make-up from, at least one of the face, the hands, the feet or the human body.

17. A method of treating at least one of sensitive skin and skin reddening of neurogenic origin in a mammal comprising administering a pharmaceutical, cosmetic, dermatological or veterinary composition which comprises an effective amount of at least one alkaline-earth metal or pharmaceutically, cosmetically, or dermatologically acceptable salt thereof wherein said alkaline-earth metal possesses TNF-alpha inhibitory activity.

18. A method of treating a pathological and/or physiological disorder associated with the release of TNF-alpha in a mammal comprising administering a pharmaceutical, cosmetic, dermatological or veterinary composition which comprises an effective amount of at least one alkaline-earth metal or a pharmaceutically acceptable salt thereof, the alkaline-earth metal moiety having TNF-alpha inhibitory activity.

19. A method of treating a disorder selected from the group consisting of rosacea, comprising administering a cosmetic, pharmaceutical, dermatological or veterinary composition comprising an effective amount of at least one alkaline-earth metal or cosmetically, pharmaceutically, or dermatologically acceptable salt thereof, the alkaline-earth metal moiety having TNF-alpha inhibitory activity.

20. Method according to claim 17, wherein the salt is selected from the group consisting of barium, calcium, magnesium, strontium and beryllium containing salts.

21. Method according to claim 18, wherein the salt is selected from the group consisting of barium, calcium, magnesium, strontium and beryllium containing salts.

22. Method according to claim 19, wherein the salt is selected from the group consisting of barium, calcium, magnesium, strontium and beryllium containing salts.

23. Method according to claim 17, wherein the salt is a magnesium or strontium containing salt.

24. Method according to claim 18, wherein the salt is a magnesium or strontium containing salt.

25. Method according to claim 19, wherein the salt is a magnesium or strontium containing salt.

26. A method of treating a disorder associated with the release of substance P comprising administering to a mammal in need of such treatment an effective amount of at least one strontium salt contained in a cosmetically, pharmaceutically, dermatologically or veterinary acceptable carrier.

27. A method of treating a condition selected from the group consisting of skin conditions, bronchopulmonary conditions, pain, gastrointestinal conditions and central nervous system disorders comprising administering to a mammal in need of such treatment an effective amount of at least one strontium salt contained in a cosmetically, dermatologically, pharmaceutically or veterinary acceptable carrier.

28. A method of treating a condition selected from the group consisting of atopic dermatitis, eczema, psoriasis and acne comprising administering to a mammal in need of such treatment an effective amount of at least one strontium salt.

29. The method of claim 17, wherein the salt is a nitrate or chloride.

30. The method of claim 18, wherein the salt is a nitrate or chloride.

31. The method of claim 19, wherein the salt is a nitrate or chloride.

32. The method of claim 26, wherein the salt is a nitrate or chloride.

33. The method of claim 27, wherein the salt is a nitrate or chloride.

34. The method of claim 28, wherein the salt is a nitrate or chloride.

35. The method of claim 29, wherein the salt is strontium nitrate or strontium chloride.

36. The method of claim 30, wherein the salt is strontium nitrate or strontium chloride.

37. The method of claim 31, wherein the salt is strontium nitrate or strontium chloride.

38. The method of claim 32, wherein the salt is strontium nitrate or strontium chloride.

39. The method of claim 33, wherein the salt is strontium nitrate or strontium chloride.

40. The method of claim 34, wherein the salt is strontium nitrate or strontium chloride.

41. The method of claim 17, wherein the amount of the salt ranges from 0.01 to 30% by weight relative to the total weight of the composition.

42. The method of claim 18, wherein the amount of the salt ranges from 0.01 to 30% by weight relative to the total weight of the composition.

43. The method of claim 19, wherein the amount of the salt ranges from 0.01 to 30% by weight relative to the total weight of the composition.

44. The method of claim 26, wherein the amount of the salt ranges from 0.01 to 30% by weight relative to the total weight of the composition.

45. The method of claim 27, wherein the amount of the salt ranges from 0.01 to 30% by weight relative to the total weight of the composition.

46. The method of claim 28, wherein the amount of the salt ranges from 0.01 to 30% by weight relative to the total weight of the composition.

47. The method of claim 41, wherein the amount of salt ranges from 0.1 to 20% by weight.

48. The method of claim 42, wherein the amount of salt ranges from 0.1 to 20% by weight.

49. The method of claim 43, wherein the amount of salt ranges from 0.1 to 20% by weight.

50. The method of claim 44, wherein the amount of salt ranges from 0.1 to 20% by weight.

51. The method of claim 45, wherein the amount of salt ranges from 0.1 to 20% by weight.

52. The method of claim 46, wherein the amount of salt ranges from 0.1 to 20% by weight.

53. The method of claim 47, wherein the amount of salt ranges from 0.5 to 10% by weight.

54. The method of claim 48, wherein the amount of salt ranges from 0.5 to 10% by weight.

55. The method of claim 49, wherein the amount of salt ranges from 0.5 to 10% by weight.

56. The method of claim 50, wherein the amount of salt ranges from 0.5 to 10% by weight.

57. The method of claim 51, wherein the amount of salt ranges from 0.5 to 10% by weight.

58. The method of claim 52, wherein the amount of salt ranges from 0.5 to 10% by weight.

59. The method of claim 17, wherein the composition further comprises at least one of mineral or thermal water.

60. The method of claim 18, wherein the composition further comprises at least one of mineral or thermal water.

61. The method of claim 19, wherein the composition further comprises at least one of mineral or thermal water.

62. The method of claim 26, wherein the composition further comprises at least one of mineral or thermal water.

63. The method of claim 27, wherein the composition further comprises at least one of mineral or thermal water.

64. The method of claim 28, wherein the composition further comprises at least one of mineral or thermal water.

65. The method of claim 17, wherein the composition is applied topically, injected or orally administered.

66. The method of claim 18, wherein the composition is applied topically, injected or orally administered.

67. The method of claim 19, wherein the composition is applied topically, injected or orally administered.

68. The method of claim 26, wherein the composition is applied topically, injected or orally administered.

69. The method of claim 27, wherein the composition is applied topically, injected or orally administered.

70. The method of claim 28, wherein the composition is applied topically, injected or orally administered.

71. Method according to claims 17, 18, 19, 26, 27 or 28, wherein the administered composition comprises an aqueous solution, oily or aqueous-alcoholic solution, a water-in-oil emulsion, an oil-in-water emulsion, a microemulsion, an aqueous gel, an anhydrous gel, a serum, a dispersion of visicles, microcapsules or microparticles.

72. Method according to claims 17, 18, 19, 26, 27 or 28, wherein the composition contains at least one agent different from said salts which is selected from the group consisting of neuropeptide antagonists, inflammation mediator antagonists, antibacterial, antiparasitic, antifungal, anti-inflammatory, antiseptic, antipruriginous, anaesthetic, antiviral, keratolytic, anti-free radical, antiseborrheic, anti-dandruff and anti-acne agents, corticoids and agents that modulate at least one of differentiation proliferation or pigmentation of the skin.

73. Method according to claim 67, wherein said agent is selected from the group consisting of anaesthetics, antiparasitic agents, non-steroidal anti-inflammatory agents, receptor antagonists of substance P, receptor antagonists of CGRP, interleukin-1 antagonists and histamine antagonists.

74. Method according to claim 67, wherein said agent comprises from 0.000001 to 10% of the total weight of the composition.

75. Method according to claims 17, 18, 19, 26, 27 or 28, wherein the composition contains, in addition, at least one active agent selected from the group consisting of proteins, protein hydrolysates, amino acids, polyols, urea, sugars, sugar derivatives, vitamins, starches, plant extracts, essential fatty acids, ceramides, essential oils and hydroxy acids.

76. Method according to claims 17, 18, 19, 26, 27 or 28, wherein the composition is provided in a form suitable for topical application.

77. Method according to claims 17, 18, 19, 26, 27, or 28, wherein the composition contains, in addition, at least one adjuvant chosen from fatty substances, silicones, hydrophilic gelling agents, lipophilic gelling agents, preservatives, perfumes, antioxidants, solvents, fillers, screening agents, odor absorbers and coloring matter.

78. A method for inhibiting at least one of the attachment, the synthesis, or the release of TNF-alpha in the skin, comprising applying to at least one of the skin, the scalp and the mucous membranes a cosmetic composition containing an effective amount at least one alkaline-earth metal salt which alkaline-earth metal inhibits TNF-alpha activity contained in a cosmetically acceptable medium.

79. A method for the cosmetic treatment of at least one of sensitive skin or skin reddening of neurogenic origin, comprising applying to at least one of the skin, the scalp or the mucous membranes, which are sensitive or are affected by rosacea or are both sensitive and affected by rosacea, a composition containing an effective amount of at least one alkaline-earth metal salt which alkaline-earth metal inhibits TNF-alpha activity in a cosmetically acceptable medium.

80. A method for the cosmetic treatment of the pruriginous symptoms of disorders or diseases of at least one of the skin or the mucous membranes, comprising applying to at least one of the skin, the scalp, and the mucous membranes a composition containing an effective amount of at least one salt of at least one alkaline-earth metal which alkaline-earth metal inhibits TNF-alpha activity contained in a cosmetically acceptable medium.

81. A method according to claims 73, 74 or 75, wherein the alkaline-earth metal salt is selected from the group consisting of chlorides, carbonates, borates, nitrates, acetates, hydoxides, sulfates, the salts of fruit acids and amino acids salts.

82. The method according to claim 76, wherein the salt is selected from the group consisting of calcium, magnesium, strontium, barium and beryllium containing salts.

83. The method according to claim 77, wherein the salt is a magnesium or strontium containing salt.

84. A method for the cosmetic treatment of a physiological disorder associated with the release of substance P, comprising applying to at least one of the skin, the scalp and the mucous membranes a composition containing an effective amount of at least one strontium salt contained in a cosmetically acceptable medium.

85. The method according to claims 73, 74 or 75, wherein the salt comprises 0.001 to 30% of the total weight of the composition.

86. The method of claim 80, wherein the salt comprises 0.01 to 20% of the total weight of the composition.

87. The method of claim 81, wherein the salt comprises from 0.5 to 10% of the total weight of the composition.

* * * * *

UNITED STATES PATENT AND TRADEMARK OFFICE
CERTIFICATE OF CORRECTION

PATENT NO. : 5,851,556
DATED : December 22, 1998
INVENTOR(S) : Lionel Breton et al.

It is certified that error appears in the above-identified patent and that said Letters Patent is hereby corrected as shown below:

Column 9,
Line 6, change "cause an inhibition" to -- reduce an inhibition --.

Signed and Sealed this

Thirtieth Day of October, 2001

*Attest:*

NICHOLAS P. GODICI

*Attesting Officer* *Acting Director of the United States Patent and Trademark Office*